United States Patent [19]
Obara

[11] Patent Number: 5,358,409
[45] Date of Patent: Oct. 25, 1994

[54] ROTARY CONNECTOR FOR FLEXIBLE ELONGATE MEMBER HAVING ELECTRICAL PROPERTIES

[75] Inventor: Robert Z. Obara, Sunnyvale, Calif.

[73] Assignee: Cardiometrics, Inc., Mountain View, Calif.

[21] Appl. No.: 114,767

[22] Filed: Aug. 31, 1993

[51] Int. Cl.$^5$ .............................................. H01R 17/18
[52] U.S. Cl. ........................................ 439/20; 439/86; 439/669; 439/909; 128/642
[58] Field of Search .................. 439/25, 24, 23, 21, 439/20, 18, 28, 481–483, 909, 912, 669, 13, 86; 128/639, 642; 607/122–125

[56] References Cited

U.S. PATENT DOCUMENTS

| | | | |
|---|---|---|---|
| 2,310,020 | 2/1943 | Gallo | 219/141 |
| 4,712,557 | 12/1987 | Harris | 439/86 |
| 4,934,367 | 6/1990 | Daglow et al. | 439/669 |
| 5,240,437 | 8/1993 | Christian | 439/668 |

Primary Examiner—Gary F. Paumen
Attorney, Agent, or Firm—Flehr, Hohbach, Test, Albritton & Herbert

[57] ABSTRACT

Rotary connector for use with a flexible elongate member having electrical properties and having a proximal extremity with at least first and second conductive spaced-apart sleeves provided thereon. A housing is provided having a bore therein. First and second spaced-apart conductive disks are disposed in said bore. The disks are adapted to have the proximal extremity of the flexible elongate member extend therethrough and to have the conductive sleeves be in contact with the conductive disks while permitting rotation of the flexible elongate member, a push button clamping assembly is carried by the housing for retaining the proximal extremity of the flexible elongate member in the housing. Leads are connected to the conductive disks.

7 Claims, 2 Drawing Sheets

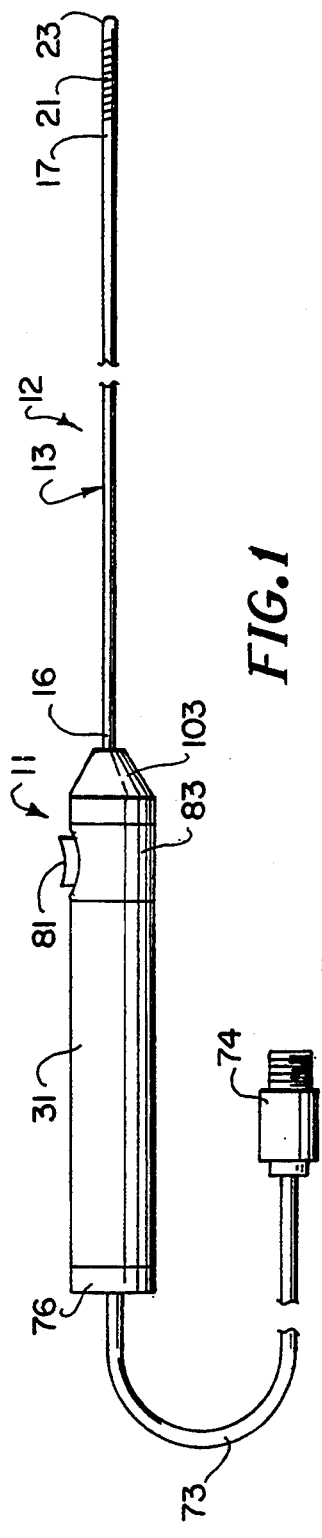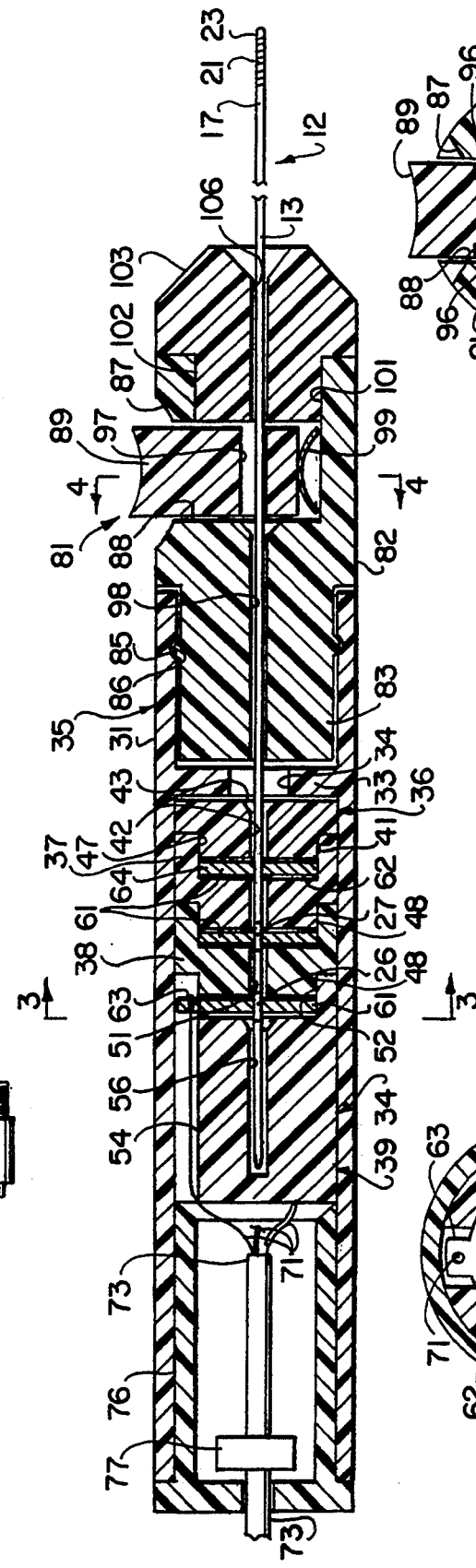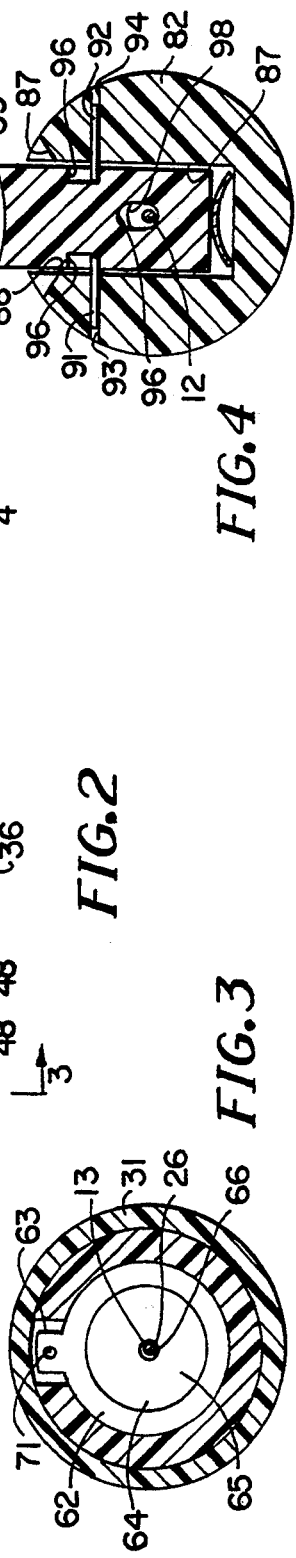

ROTARY CONNECTOR FOR FLEXIBLE ELONGATE MEMBER HAVING ELECTRICAL PROPERTIES

This invention relates to a rotary connector for a flexible elongate member having electrical properties and more particularly to a rotary connector for a flexible elongate member having electrical properties and having a proximal extremity with at least first and second conductive sleeves provided thereon.

In patent application Ser. No. 07/904,831, filed on Jun. 26, 1992, now U.S. Pat. No. 5,240,437, issued Aug. 31, 1993, there is disclosed a torquable guide wire assembly with electrical functions which is provided with a rotary connector. With such a rotary connector, it has been found that on occasion when contamination is present, as for example a blood or saline solution, there is a tendency for intermittent electrical contact to occur. There is therefore need to overcome such possible intermittent contact and to ensure continuous contact.

In general, it is an object of the present invention to provide a rotary connector for use with a flexible elongate member having electrical properties which provides a consistent electrical contact.

Another object of the invention is to provide a connector of the above character which provides very low friction against rotation of the flexible elongate element.

Another object of the invention is to provide a connector of the above character in which the proximal extremity of the flexible elongate element can be readily inserted and removed.

Another object of the invention is to provide the connector of the above character which includes means for retaining the proximal extremity of the flexible elongate member in the connector.

Additional objects and features of the invention will appear from the following description in which the preferred embodiments are set forth in detail in conjunction with the accompanying drawings.

FIG. 1 is a side-elevational view of a rotary connector incorporating the present invention and having a flexible elongate member mounted therein.

FIG. 2 is longitudinal cross-sectional view of the connector shown in FIG. 1.

FIG. 3 is a cross-sectional view taken along the line 3—3 of FIG. 1.

FIG. 4 is a cross-sectional view taken along the line 4—4 of FIG. 1.

Figure 5:
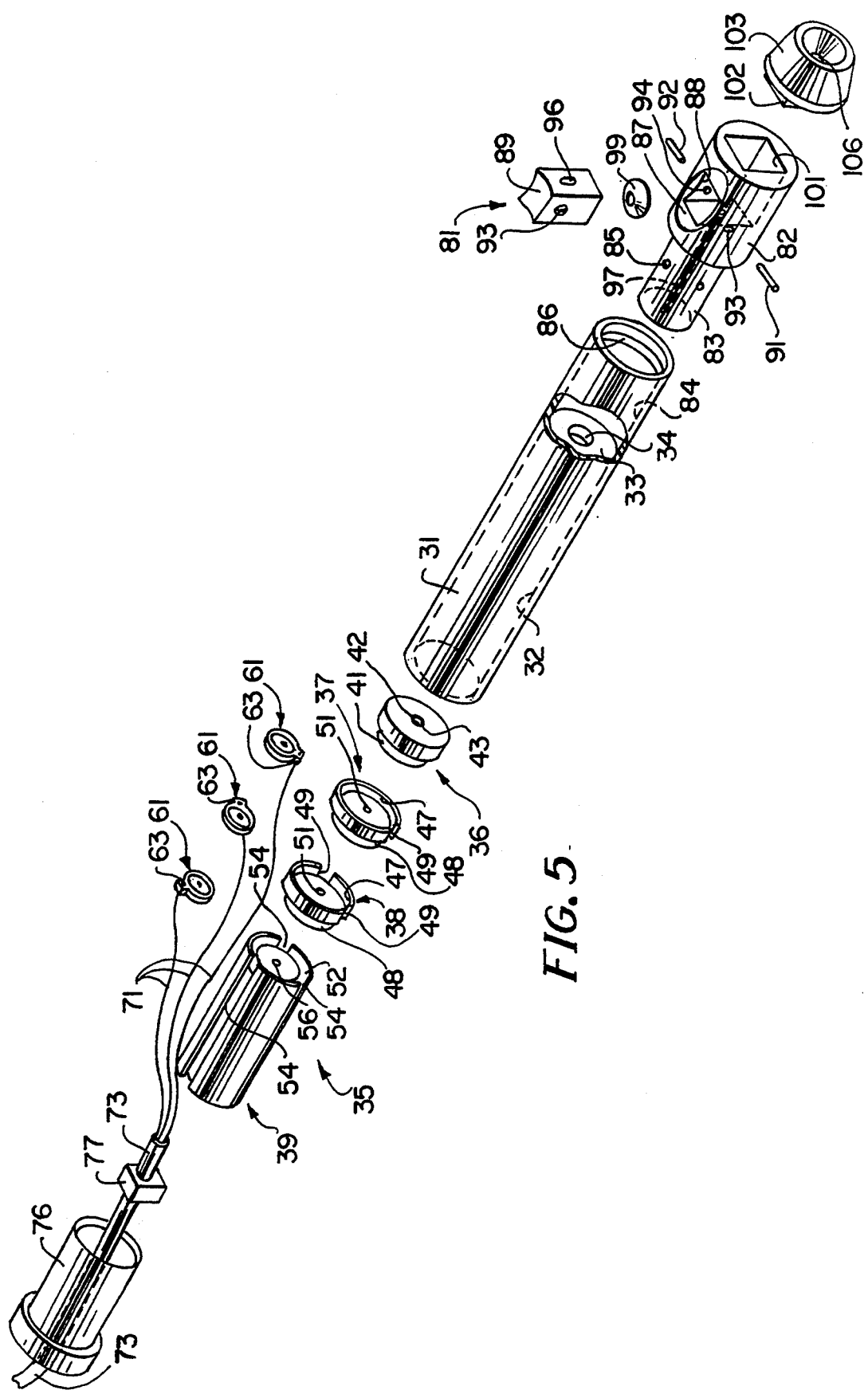
FIG. 5 is an exploded isometric view of the rotary connector shown in FIG. 1.

In general, the rotary connector incorporated in the present invention is for use with a flexible elongate member having electrical properties and having a proximal extremity with at least first and second conductive sleeves provided thereon. An outer housing is provided which has a bore therein. First and second spaced-apart conductive disks are mounted in the bore. The conductive disks are sized so that the conductive sleeves can extend therethrough and make electrical contact therewith. Leads are coupled to the conductive disks. A gripping mechanism is carried by the housing for retaining the proximal extremity of the flexible elongate member in the housing.

More in particular, as shown in the drawings, the rotary connector 11 is adapted to be used with a flexible elongate member 12 which can be in the form of a guide wire. The flexible elongate member 12 is provided with a shaft 13 formed of a stainless steel hypotube and having proximal and distal extremities 16 and 17. A coil spring 21 is mounted on the distal extremity 17 and is secured thereto. It carries a housing (not shown) which carries an electrical device 23 such as an ultrasonic transducer. Conductors (not shown) are connected to the electrical device 23 such as to the front and back sides of the ultrasonic transducer 23 and extend through the coil spring 21 and through the shaft 13 to the proximal extremity and are connected to first and second conductive sleeves or slip rings 26 and 27.

The rotary connector 11 consists of a shell or outer housing 31 which is cylindrical in shape which is provided with a bore 32 extending therethrough up to a dam 33. The dam 33 has a centrally disposed hole 34 therein. A multistage inner housing 35 is mounted within the shell 31. The outer housing 31 and the multistage inner housing 35 are formed of a suitable material such as plastic. The multistage inner housing 35 consists of a first stage 36, a second stage which consists of two pieces 37 and 38 and a third stage 39.

The first stage 36 is formed of a solid piece and is provided with an annular recess 41. It is also provided with a chamfered hole 42 extending therethrough which is sized so that it is adapted to accommodate the proximal extremity of the flexible elongate member 12 which can be considered to be a male connector. A chamfer or countersink 43 is provided at the commencement of the hole 42 to facilitate the introduction of the proximal extremity of the flexible elongate member 12 therethrough. The first stage 36 has a diameter such that it can be introduced into the bore 32 of the shell or outer housing 31 with the hole 42 being axially aligned with the axis of the housing 31.

The second stage pieces 37 and 38 are also formed of a solid material and are provided with bores 47 on the distal ends and annular recesses 48 on the proximal ends and slots 49 extending into the bores 47 as shown particularly in FIG. 5 with the slot 49 in piece 37 being offset circumferentially with respect to the slot 49 in piece 38 by a suitable angle such as 120°. Chamfered holes 51 extend axially of the second stage pieces 37 and 38. The bores 47 and the annular recesses 48 are sized so that the second stage pieces 37 and 38 can be nested and seated in the bore 32 of the housing 31 as shown in FIG. 2.

The third stage 39 is also formed of a solid piece and is provided with a central bore 52 and is also provided with three circumferentially spaced apart slots 54 spaced 120° apart. The bore 52 is sized so that second stage piece 38 can seat in the bore 52. A plurality of circumferentially spaced-apart slots 54 spaced approximately 120° apart are provided in the third stage 39 and extend longitudinally thereof and open into the annular recess 52. A chamfered hole 56 extends through the third stage 39 and is axially aligned with the chamfered holes 51 in second stage pieces 37 and 38. The plastic which is used for the various parts of the rotary connector 11 can be of a suitable type such as ABS.

Conductive disks 61 are provided which are adapted to be mounted in the bores 47 of the second stage pieces 37 and 38 and in the bore 52 of the third stage 39. Each of the conductive disks 61 consists of a conductive metal ring 62 formed of a suitable material such as brass which is provided with an integral tab 63 and has a centrally disposed opening 64 therein. A conductive elastomeric membrane 65 is vulcanized to the ring 62 and extends across the opening 64 in the ring. One conductive elastomeric material found to be satisfactory is an electrically conductive silicon rubber identified as X-65-101U supplied by the Performance Elastomers division of Furon, 1032 Morse Avenue, Sunnyvale, Calif., 94089. Such an elastomer has a Shore A hardness of 58, a tensile strength of 250 psi, elongation of 200%, a volume resistivity in ohm-cm of 0.006 and a tear strength of 60 psi. It is desirable that the conductivity of the material used for the membrane be very high so as to make excellent electrical contact with the conductive slip ring when it is disposed in the membrane. Thus it can be less than 0.006 ohm-cm. The material should not be brittle but it should be flexible enough so that it can withstand puncturing without ripping or tearing. Typically the membrane before vulcanization can have a thickness ranging from 0.005–0.040 inches and preferably ranging from 0.025–0.030 inches. The ring 62 itself can have an outside diameter of a suitable size, as for example 0.25 inches. If desired, a small centrally disposed hole 66 can be provided in each of the membranes 65 through which the proximal extremity 16 of the flexible elongate member 12 can pass. It is desirable that this hole have a diameter which is smaller than the diameter of the conductive sleeves or slip rings 26 so that an elastomeric fit will occur between the membrane 65 and the slip ring 26 when it is disposed therein to provide good conductivity with the slip ring.

Conductors 71 are provided which are connected to the tabs 63 of the conductive rings 62, which tabs are aligned with one of the slots 49 with the conductors extending proximally therefrom through the slots 49 and the slots 54. The conductors 71 extend proximally and are connected into a cable 73 which extends through a strain relief such as cable clip 77 mounted within a flanged end cap 76. The cable 73 extends through the end cap 76 and is connected to a fitting 74 (see FIG. 1) which is adapted to be connected to electronic equipment (not shown).

The conductive disks 61 are adapted to be disposed within the bores 47 and 52 and are retained therein with the tabs 63 being aligned with one of the tabs 63 being disposed in each of the circumferentially spaced-apart slots 49 and 54. All of the stages can then be assembled into a single unit and then placed within the outer housing or shell 31 followed by the cable 73 and the cable clip 77 and the end cup 76 to close off on one end of the outer housing or shell 31. Means is carried by the outer housing 31 for retaining the proximal extremity of the flexible elongate member 12 in a fixed longitudinal position within the outer housing or shell 31 after the proximal extremity 16 has been positioned in the conductive disks 61 disposed within the outer housing or shell 31. This means takes the form of a push button grip mechanism 81. It consists of a spindle 82 formed of a suitable material such as plastic which is provided with a cylindrical extension 83 of reduced diameter which is adapted to fit in a bore 84 within the distal extremity of the outer housing or shell 31 on the other side of the dam 33. In order to reduce the friction during rotation of the spindle 82 the cylindrical extension 83 is spaced from the dam 33 and is provided with rounded circumferentially spaced-apart protrusions 85 which are adapted to be seated within and travel in an annular groove 86 provided in the interior wall forming the bore 84 of the outer housing 31. The spindle 82 is provided with an oval-shaped rounded depression 87. A cylindrical recess or well 88 which can be rectangular in cross section extends into the spindle 82 diametrically thereof and opens through the depression 87. A push button 89 is disposed within the recess 88. The push button 89 has an outer extremity which is in the form of a square prism shape disposed in the depression 87 to aid in sensing the push button 89 by a finger of the hand without slipping of the finger of the hand on the push button.

Means is provided for retaining the push button 89 within the recess 88 but permitting axial movement of the push button in the recess 88 and consists of first and second dowel pins 91 and 92 extending through the holes 93 and 94 in spindle 82 and having their inner extremities disposed in longitudinally extending recesses 96 provided in opposite sides of the push button 89. An elongate hole 97 is provided in the push button and extends longitudinally of the push button. The elongate hole 96 is in alignment with a hole 98 extending at right angles thereto in the spindle 82. Yieldable spring means is provided within the well 87 and consists of a dish-shaped spring member 99 disposed in the well or recess 88 and engaging the innermost extremity of the push button 89. The distal extremity of the spindle 82 is provided with a recess 101 which is rectangular in cross section that is adapted to receive a rectangular extension 102 provided on a front cap or nose piece 103. The nose piece 103 is provided with a chamfered hole 106 which is in alignment with the hole 96 and also in axial alignment with the hole 97 in the spindle 82.

Operation and use of the rotary connector 11 in connection with the flexible elongate member 12 may now be briefly described as follows. Let it be assumed that it is desired to utilize a flexible elongate member 12 such as a guide wire 12 in connection with an angioplasty procedure. Let it also be assumed that it is desired to advance the guide wire through the femoral artery into a vessel in the heart. The guide wire 12 is advanced in a conventional manner until it is near the heart. Thereafter to advance the guide wire 12 into a vessel of the heart, it is often desirable to provide means to provide rotation of the guide wire. When this is desirable, the rotary connector 11 of the present invention can be utilized. The proximal extremity 16 of the guide wire 12 can be introduced into the chamfered hole 106 provided in the nose piece 103. The proximal extremity 16 is then advanced through the elongate hole 96. While depressing the push button 89 the proximal extremity 16 is advanced through the hole 97 and thence into the hole 42 in the first stage 36, and thence through the membrane 65 of the first conductive disk 61, thence through the hole 51, thence through the next conductive disk 61 through the hole 51, thence through the last conductive disk 61, thence through the hole 56 in the third stage 39 and until it is seated at the bottom of the hole 56. The slip rings 26 and 27 are then in alignment with the conductive disks 61 and make electrical contact therewith through their conductive membranes 65 and through the conductive ring 62 to the conductors 71 and thence into the cable 73 and the connector 74. One of the disks 61 makes contact with shaft 13 to form a ground connection.

As soon as the proximal extremity 16 has been firmly seated within the rotary connector 11, the push button 89 can be released to permit the spring member 99 to urge the button 89 upwardly to have the bottom of the hole 97 engage the proximal extremity 16 and to clamp it against the holes 106 and 98. Thereafter, the spindle 82 can be rotated to rotate the flexible elongate element 12 to any desired angular position while still maintaining electrical contact therewith through the conductive disks 61.

The guide wire can then be advanced and rotated until the distal extremity has been advanced into the desired location in the blood vessel. In connection with the procedure, if it is necessary to use an exchange wire, the rotary connector 11 can be readily removed by depressing the push button 89 to release the proximal extremity 16 of the flexible elongate member 12 to permit the same to be removed. An exchange wire can then be affixed thereto. Thereafter, the angioplasty procedure can be completed in a conventional manner.

From the foregoing it can be seen that there has been provided a rotary connector which provides continuous electrical contact with the slip rings during rotation of the flexible elongate member even in the presence of contamination. It is relatively simple and is easy to operate and can be operated by one hand with the finger depressing the push button while permitting use of the other hand to insert the proximal extremity of the guide wire into the rotary connector.

What is claimed is:

1. A rotary connector for use with a flexible elongate member having electrical properties and having a proximal extremity with at least first and second spaced-apart conductive sleeves provided thereon comprising a housing having a bore therein, first and second spaced-apart conductive disks disposed in said bore, said conductive disks being adapted to have said proximal extremity extend therethrough and to have said conductive sleeves be in contact with the conductive disks while permitting substantially free rotation of the flexible elongate member, means carried by the housing adapted to retain the proximal extremity of the flexible elongate member in the housing against a moderate pull on the flexible elongate member, and leads connected to the conductive disks.

2. A rotary connector as in claim 1 wherein said means carried by the housing adapted to retain the proximal extremity of the flexible elongate member in the housing includes a gripping mechanism separate from the conductive disks carried by the housing for retaining the proximal extremity of the flexible elongate member in the housing.

3. A rotary connector as in claim 1 wherein said conductive disks are formed of a metallic conducting ring having an opening therein and a conductive elastomer membrane extending over the opening in said ring.

4. A rotary connector as in claim 3 wherein said conductive elastomer membrane has a thickness ranging from 0.005–0.040 inches.

5. A rotary connector as in claim 4 wherein said conductive elastomer membrane is formed with a small diameter opening having a size which is less than the size of the conductive sleeve to be disposed therein.

6. A rotary connector as in claim 2 wherein said gripping mechanism includes a spindle rotatably mounted in the housing and having a diametrically extending well, a push button mounted in the well in the spindle for movement diametrically of the spindle, means for limiting the movement of the push button in and out of the well, and means disposed in the well yieldably urging the push button out of the well.

7. A rotary connector as in claim 6 wherein said push button is provided with an elongate slot adapted to receive the proximal extremity of the flexible elongate member wherein said spindle is provided with a hole extending therethrough and in registration with said slot.

* * * * *